(12) United States Patent
Muharemovic et al.

(10) Patent No.: US 8,724,542 B2
(45) Date of Patent: May 13, 2014

(54) TRANSMISSION USING NESTED OFDMA (75) Inventors: Tarik Muharemovic, Dallas, TX (US); Zukang Shen, Richardson, TX (US); Jing Jiang, Allen, TX (US)

(73) Assignee: Texas Instruments Incorporated, Dallas, TX (US)

( * ) Notice: Subject to any disclaimer, the term of this patent is extended or adjusted under 35 U.S.C. 154(b) by 174 days.

(21) Appl. No.: 12/858,944

(22) Filed: Aug. 18, 2010

(65) Prior Publication Data

US 2010/0309775 A1 Dec. 9, 2010

Related U.S. Application Data

(62) Division of application No. 12/185,531, filed on Aug. 4, 2008, now abandoned.

(60) Provisional application No. 60/954,859, filed on Aug. 9, 2007, provisional application No. 60/955,671, filed on Aug. 14, 2007, provisional application No. 60/956,946, filed on Aug. 21, 2007.

(51) Int. Cl.
*H04B 7/212* (2006.01)

(52) U.S. Cl.
USPC ........... 370/321; 370/326; 370/330; 370/337; 370/344; 370/347; 370/442; 370/458; 370/478; 370/480

(58) Field of Classification Search
USPC ................. 370/319, 321, 326, 330, 336, 337, 370/343–347, 442, 458, 478, 480
See application file for complete search history.

(56) References Cited

U.S. PATENT DOCUMENTS

| 7,020,218 | B2 | 3/2006 | Arnesen |
| 2004/0258014 | A1 | 12/2004 | Ro et al. |
| 2006/0268671 | A1* | 11/2006 | Coon ............................ 370/203 |
| 2006/0291372 | A1 | 12/2006 | Koo et al. |
| 2007/0058595 | A1 | 3/2007 | Classon et al. |
| 2007/0127248 | A1* | 6/2007 | Egashira et al. .............. 362/351 |
| 2009/0041092 | A1 | 2/2009 | Kim et al. |

OTHER PUBLICATIONS

Texas Instruments, "Uplink Reference Signals in Support of Requirements for High-Speed UEs", 3GPP TSG RAN WG1 #50, R1-073420, Agenda Item: 7.2.2, Athens, Greece, Aug. 20-24, 2007, pp. 1-5.

* cited by examiner

*Primary Examiner* — Alvin Zhu
(74) *Attorney, Agent, or Firm* — Ronald O. Neerings; Wade James Brady; Frederick J. Telecky, Jr.

(57) ABSTRACT

A transmission of information within a wireless cellular network may include a first and second group of samples. A first group of samples is created comprising at least a first and a last subgroup, wherein the last subgroup is same as the first subgroup. A second group of samples created. A transformed set of samples produced by jointly transforming the created first and second group with a discrete Fourier transform (DFT). The transformed set of samples is expanded to produce an expanded set, and the expanded set is transformed with an inverse discrete Fourier transform (IDFT) to produce an OFDM symbol with a fractional payload. The first group of samples is a reference signal (RS), which is known to the receiver before the transmission occurs, while the second group of samples is information data.

51 Claims, 9 Drawing Sheets

TRANSMISSION USING NESTED OFDMA

CLAIM OF PRIORITY

This application is a divisional application of U.S. patent application Ser. No. 12/185,531 filed Aug. 4, 2008, now abandoned. This application for Patent claims priority to U.S. Provisional Application No. 60/954,859 entitled "Derived PUSCH Slot Structure for High-Speed UEs" filed Aug. 9, 2007, incorporated by reference herein. This application for Patent also claims priority to U.S. Provisional Application No. 60/955,671 entitled "Uplink Reference Signals in Support of Requirements for High-Speed UEs" filed Aug. 14, 2007, incorporated by reference herein. This application for Patent also claims priority to U.S. Provisional Application No. 60/956,946 entitled "Nested Multi-Rate OFDMA System" filed Aug. 21, 2007, incorporated by reference herein.

FIELD OF THE INVENTION

This invention generally relates to wireless cellular communication, and in particular to a slot structure for use in orthogonal frequency division multiple access (OFDMA), DFT-spread OFDMA, and single carrier frequency division multiple access (SC-FDMA) systems.

BACKGROUND OF THE INVENTION

Wireless cellular communication networks incorporate a number of mobile UEs and a number of NodeBs. A NodeB is generally a fixed station, and may also be called a base transceiver system (BTS), an access point (AP), a base station (BS), or some other equivalent terminology. As improvements of networks are made, the NodeB functionality evolves, so a NodeB is sometimes also referred to as an evolved NodeB (eNB). In general, NodeB hardware, when deployed, is fixed and stationary, while the UE hardware is portable.

In contrast to NodeB, the mobile UE can comprise portable hardware. User equipment (UE), also commonly referred to as a terminal or a mobile station, may be fixed or mobile device and may be a wireless device, a cellular phone, a personal digital assistant (PDA), a wireless modem card, and so on. Uplink communication (UL) refers to a communication from the mobile UE to the NodeB, whereas downlink (DL) refers to communication from the NodeB to the mobile UE. Each NodeB contains radio frequency transmitter(s) and the receiver(s) used to communicate directly with the mobiles, which move freely around it. Similarly, each mobile UE contains radio frequency transmitter(s) and the receiver(s) used to communicate directly with the NodeB. In cellular networks, the mobiles cannot communicate directly with each other but have to communicate with the NodeB.

Control information bits are transmitted, for example, in the uplink (UL), for several purposes. For instance, Downlink Hybrid Automatic Repeat ReQuest (HARQ) requires at least one bit of ACK/NACK transmitted in the uplink, indicating successful or failed circular redundancy check(s) (CRC). Moreover, a one bit scheduling request indicator (SRI) is transmitted in uplink, when UE has new data arrival for transmission in uplink. Furthermore, an indicator of downlink channel quality (CQI) needs to be transmitted in the uplink to support mobile UE scheduling in the downlink. While CQI may be transmitted based on a periodic or triggered mechanism, the ACK/NACK needs to be transmitted in a timely manner to support the HARQ operation. Note that ACK/NACK is sometimes denoted as ACKNAK or just simply ACK, or any other equivalent term. As seen from this example, some elements of the control information should be provided additional protection, when compared with other information. For instance, the ACK/NACK information is typically required to be highly reliable in order to support an appropriate and accurate HARQ operation. This uplink control information is typically transmitted using the physical uplink control channel (PUCCH), as defined by the 3GPP working groups (WG), for evolved universal terrestrial radio access (EUTRA). The EUTRA is sometimes also referred to as 3GPP long-term evolution (3GPP LTE). The structure of the PUCCH is designed to provide sufficiently high transmission reliability.

In addition to PUCCH, the EUTRA standard also defines a physical uplink shared channel (PUSCH), intended for transmission of uplink user data. The Physical Uplink Shared Channel (PUSCH) can be dynamically scheduled. This means that time-frequency resources of PUSCH are re-allocated every sub-frame. This (re)allocation is communicated to the mobile UE using the Physical Downlink Control Channel (PDCCH). Alternatively, resources of the PUSCH can be allocated semi-statically, via the mechanism of persistent scheduling. Thus, any given time-frequency PUSCH resource can possibly be used by any mobile UE, depending on the scheduler allocation. Physical Uplink Control Channel (PUCCH) is different than the PUSCH, and the PUCCH is used for transmission of uplink control information (UCI). Frequency resources which are allocated for PUCCH are found at the two extreme edges of the uplink frequency spectrum. In contrast, frequency resources which are used for PUSCH are in between. Since PUSCH is designed for transmission of user data, re-transmissions are possible, and PUSCH is expected to be generally scheduled with less stand-alone sub-frame reliability than PUCCH. The general operations of the physical channels are described in the EUTRA specifications, for example: "$3^{rd}$ Generation Partnership Project; Technical Specification Group Radio Access Network; Evolved Universal Terrestrial Radio Access (E-UTRA); Physical Channels and Modulation (Release 8)."

A reference signal (RS) is a pre-defined signal, pre-known to both transmitter and receiver. The RS can generally be thought of as deterministic from the perspective of both transmitter and receiver. The RS is typically transmitted in order for the receiver to estimate the signal propagation medium. This process is also known as "channel estimation." Thus, an RS can be transmitted to facilitate channel estimation. Upon deriving channel estimates, these estimates are used for demodulation of transmitted information. This type of RS is sometimes referred to as De-Modulation RS or DM RS. Note that RS can also be transmitted for other purposes, such as channel sounding (SRS), synchronization, or any other purpose. Also note that Reference Signal (RS) can be sometimes called the pilot signal, or the training signal, or any other equivalent term.

BRIEF DESCRIPTION OF THE DRAWINGS

Particular embodiments in accordance with the invention will now be described, by way of example only, and with reference to the accompanying drawings.

DETAILED DESCRIPTION OF EMBODIMENTS OF THE INVENTION

Figure 1:
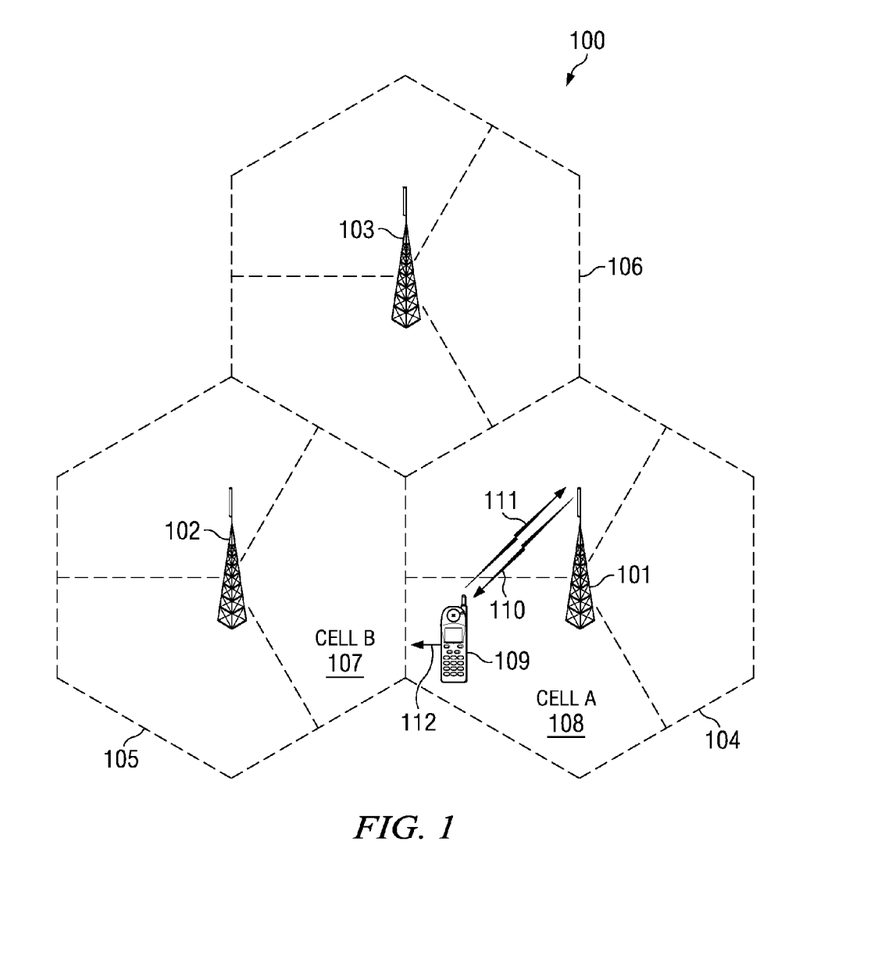
FIG. 1 is a pictorial of an illustrative telecommunications network that employs an embodiment of a slot structure using one or more fractional payload symbols to convey data information and reference signal information.

FIG. 1 shows an exemplary wireless telecommunications network 100. The illustrative telecommunications network includes representative base stations 101, 102, and 103; however, a telecommunications network necessarily includes many more base stations. Each of base stations 101, 102, and 103 are operable over corresponding coverage areas 104, 105, and 106. Each base station's coverage area is further divided into cells. In the illustrated network, each base station's coverage area is divided into three cells. Handset or other UE 109 is shown in Cell A 108, which is within coverage area 104 of base station 101. Base station 101 is transmitting to and receiving transmissions from UE 109 via downlink 110 and uplink 111. As UE 109 moves out of Cell A 108, and into Cell B 107, UE 109 may be handed over to base station 102. Because UE 109 is synchronized with base station 101, UE 109 must employ non-synchronized random access to initiate handover to base station 102.

A UE in a cell may be stationary such as within a home or office, or may be moving while a user is walking or riding in a vehicle. UE 109 moves within cell 108 with a velocity 112 relative to base station 102.

In high-Doppler environments such as when the UE is moving at a high velocity relative to the base station, the EUTRA UL link performance suffers from serious performance degradations. The reason for such degradations is that the rate of RS transmission struggles to cope with fast changes of the channel. For example, in high-Doppler environments, a channel at one end of the slot has little correlation with the channel at the other end of the slot, and thus, applying a single channel estimate for data demodulation becomes increasingly problematic as the UE speed grows.

Figure 2:
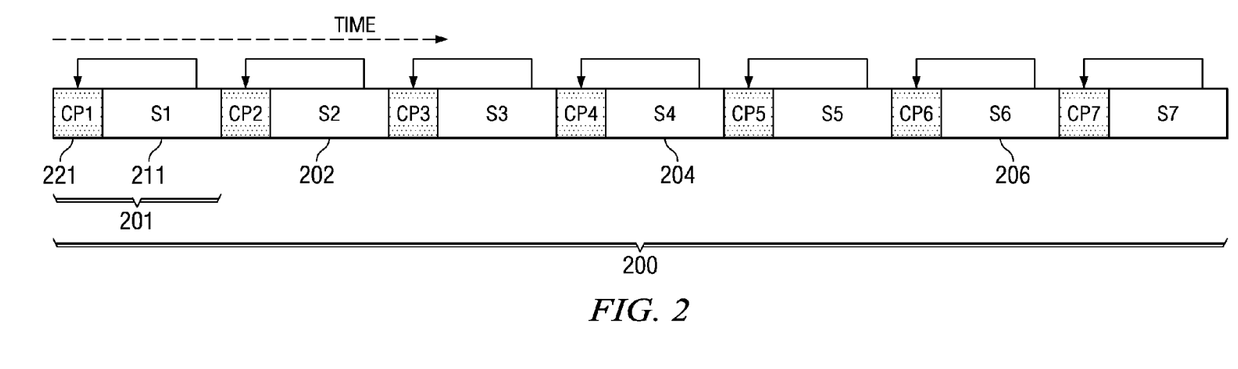
FIG. 2 is an illustration of a slot structure used for transmission in the PUSCH of FIG. 1.

FIG. 2 is an illustration of a slot structure 200 used for transmission in the PUSCH of FIG. 1. There are seven SC-OFDMA symbols S1-S7, indicated generally at 201, which are realized through a DFT-spread OFDMA transmission. Slot 200 duration is 0.5 ms. All blocks 211 are preceded by a cyclic prefix transmission 221 to protect the corresponding data 211 against channel delay spread and the respective multi-path propagation. For low-speed UEs, a reference signal (RS) may be located in symbol S4 204, and is based on Zadoff-Chu CAZAC sequences.

As used herein, the term "channel", "block," and "OFDMA symbol" all generally refer to each of the seven information carrying portions 201 of slot structure 200.

As optimized for the low-speed UEs, the RS can be positioned in the middle of the slot, inside S4 204. The link performance of such a set-up is good for low-speed mobiles, while, for high-speed mobiles, it suffers from link-level performance degradations. Link-level losses become apparent starting at around 200 kmh and 2 GHz carrier frequency. There are few options to consider for high-speed mobiles that maintain the structure of FIG. 2. One option, referred to as a baseline option, is to disregard performance degradation at high speeds and to use a common RS location for both high and low speed UEs. This RS location occupies the entire 4-th OFDM symbol (S4) 204 in the slot structure, as in FIG. 2.

Another option would be to have a configuration of the slot structure of FIG. 2 in which a second RS is added for high-speed mobiles. The problem with this option is the RS overhead. Essentially, by introducing an additional RS overhead of an entire OFDM symbol for high-speed mobiles, the UE throughput would drop by about 20%, since there would be only five instead of six data-bearing OFDM symbols.

Figure 3:
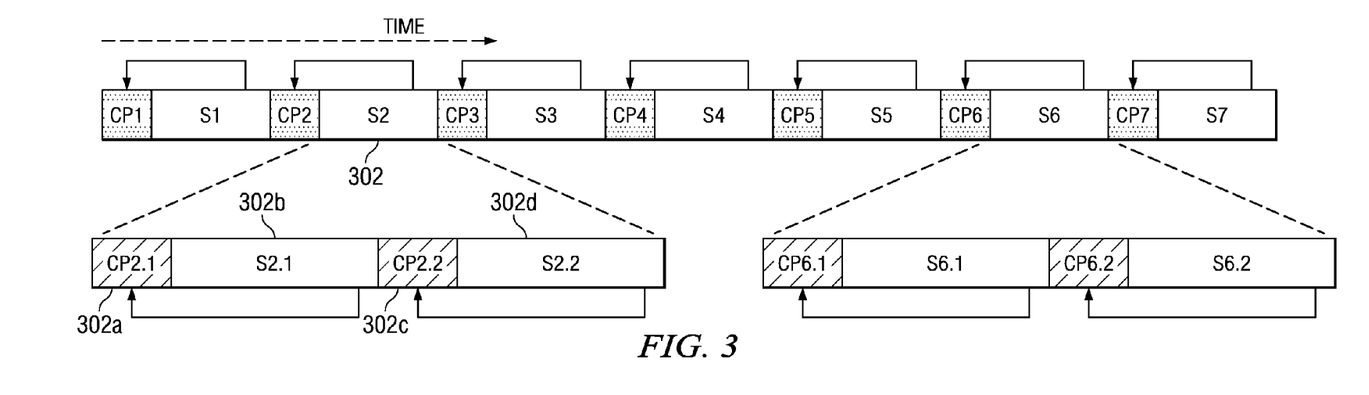
FIG. 3 is a more detailed illustration of the slot structure of FIG. 2 illustrating fractional payload symbols to convey data information and reference signal information.
Figure 6:
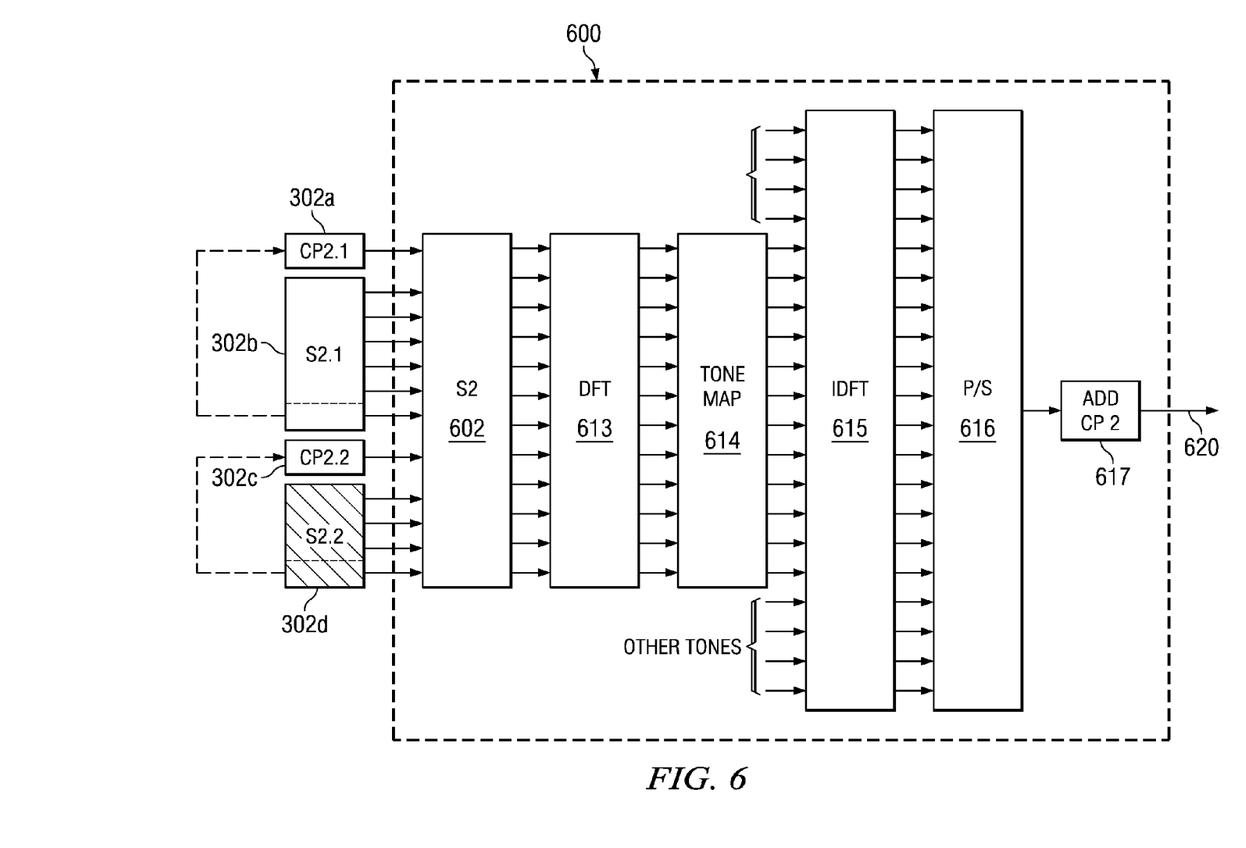
FIG. 6 is a block diagram of a transmitter for the structure of FIG. 2 illustrating insertion of RS in a fractional payload symbol.

A better option is to piggy-back an RS symbol with the data transmission in a portion of SC-OFDMA symbol. By doing this, the throughput degradation due to high UE speed can be completely avoided. This can be achieved while keeping the single-carrier property of the uplink transmission, as will be described in more detail below. Instead of adding an entire second RS symbol, an RS signal is piggy-backed with data in S2 202 and S6 206. For example, consider the symbol S2, which is transmitted using SC-OFDMA transmission. FIG. 3 is a more detailed illustration of the slot structure of FIG. 2 illustrating fractional payload symbols to convey data information and reference signal information. The symbol S2 may be divided into four parts 302a-302d; CP2.1, S2.1, CP2.2, and S2.2, respectively. These four parts collectively comprise S2. Note, this division is performed prior to a DFT modulation process, which is described later with respect to FIG. 6. The portion S2.1 is a data-bearing part, whereas CP2.1 is a cyclic prefix to S2.1, as defined before the DFT. Part S2.2 is the reference signal (RS), of whose cyclic prefix is CP2.2, also defined before the DFT, as shown in FIG. 6. In another embodiment, either or both cyclic prefixes CP2.1 and CP2.2 may alternatively be a simple guard-time, as long as the configuration is known to both the transmitter and the receiver.

The purpose of CP2.1 and the CP2.2 is to shield S2.1 and S2.2 against multi-path propagation and spill-over effects. This is achieved since S2 is basically a signal in the time-domain. As emphasized earlier, the reference signal is positioned inside S2.2. Note that the aggregate S2 302 can be regarded just as any other SC-OFDMA symbol, except that its components are now specifically defined. Thus the low PAPR (peak to average power ratio) property (single-carrier property) is maintained with this option. Clearly, duration of each of components could be any fraction of duration of S2; however, the chosen fractional duration must be known to both the transmitter and the receiver. In one embodiment, the following fractional partition is used:

Length of S2.1 equals half of the length of S2.
Length of S2.2 equals a third of the length of S2. "First" RS is placed here.
Length of CP2.1 equals one twelve-th of the length of S2
Length of CP2.2 equals one twelve-th of the length of S2
Since $1=\frac{1}{2}+\frac{1}{3}+\frac{1}{12}+\frac{1}{12}$, the entire duration of S2 is spanned. S6 is partitioned in a similar proportion, except that, due to mirror-symmetry, the following partition is applied:

Length of S6.1 equals a third of the length of S6. "Second" RS is placed here.

Length of S6.2 equals a half of the length of S6.

Length of CP6.1 equals one twelve-th of the length of S6.

Length of CP6.2 equals one twelve-th of the length of S6.

For this embodiment in which the time length of slot structure 200 is 0.5 ms, since worst-case delay spread (5 μsec) is less than one twelfth of the OFDM symbol duration (66.7 μsec), the CP2.1 and CP2.2 provide a sufficient guard (also CP6.1 and CP6.2). Data-bearing samples S2.1 and S6.2 collectively carry enough data as a single SC-OFDMA symbol, and thus, when combined with S1, S3, S4, S5, and S7, the amount of channel bits carried by high-speed UEs is the same as the amount of channel bits carried by the low-speed UEs, which use a sole RS is S4. Thus, there are no rate-matching issues. Finally, since the length of S2 is a multiple of 12, and of {2, 3, 5}, the length of each of the non-prefix components S2.1 and S2.2 remains a multiple of {2, 3, 5} as permissible by the EUTRA DFT sizes numerology. It is important to note that cyclic prefixes {CP1, CP2, . . . , CP7} to full OFDM symbols {S1, S2, . . . , S7} are added after the IDFT, whereas cyclic prefixes {CP2.1, CP2.2, S6.1, S6.2} are added before the DFT, as illustrated in FIG. 4 and as will be explained in more detail later.

Figure 4:
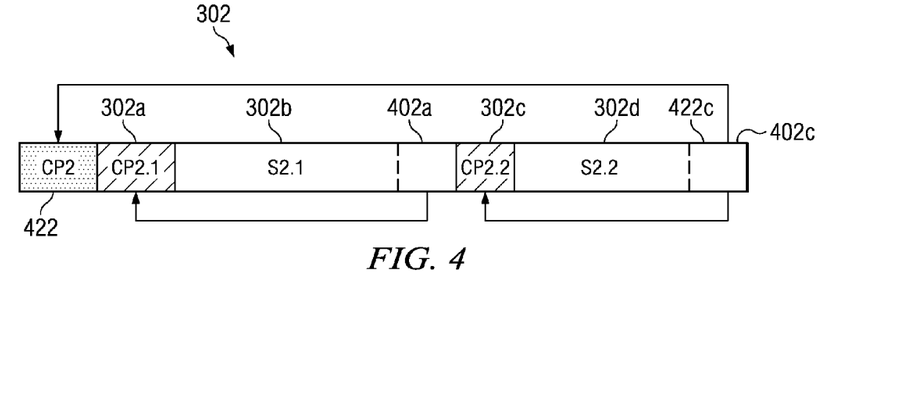
FIG. 4 is a detail of one fractional payload symbol.

FIG. 4 is a detail of one fractional payload symbol 302, as illustrated in FIG. 3. Formation of CP2.1 (302a) may be done by simply taking a portion of fractional symbol S2.1 indicated at 402a and repeating it as the cyclic prefix 302a prior to the DFT operation. Similarly, a portion of fractional symbol S2.2 indicated at 402c in repeated as cyclic prefix 302c prior to the DFT operation. After the IDFT operation, a portion of symbol 302 indicated at 422c may be repeated as cyclic prefix 422. Portion 422c may be the same size as portion 402c in one embodiment, but may be different sizes in another embodiment.

Figure 5:
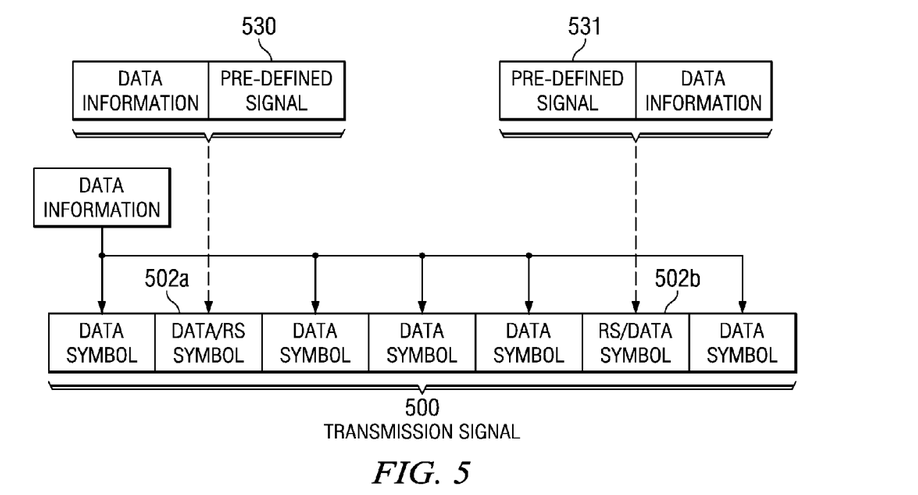
FIG. 5 is a pictorial illustration the slot structure of FIG. 2 illustrating fractional payload symbols to convey data information and reference signal information.

FIG. 5 is a pictorial illustration the slot structure of FIG. 2 illustrating transmission signal 500 with fractional payload symbols 502a, 502b to convey data information and reference signal information 530, 531 respectively. For an extended CP slot format, with only 6 OFDM symbols, the symbols S2 and S5 can piggy-back the RS. In this manner, a 0.5 ms slot structure is produced that contains at least two OFDM symbols each with fractional payload containing reference signals (RS) and comprising a number of OFDM symbols with integral payload wherein the number is selected from the set {4,5}.

FIG. 6 is a block diagram of a DFT-spread OFDMA modulator for the structure of FIG. 2 illustrating insertion of an RS in a fractional payload symbol. As described above, in this embodiment the symbol S2 is divided into four parts 302a-302d; S2.1, CP2.1, S2.2, and CP2.2, respectively. These four parts collectively comprise an S2 signal 602. Note, this division is performed prior to a DFT modulation process 613. The portion S2.1 is a data-bearing part, whereas CP2.1 is a cyclic prefix to S2.1, as defined before the DFT. Part S2.2 is the reference signal (RS), of whose cyclic prefix is CP2.2, also defined before the DFT, as shown in FIG. 6. In another embodiment, either or both cyclic prefixes CP2.1 and CP2.2 may alternatively be a simple guard-time, as long as the configuration is known to both the transmitter and the receiver.

Discrete Fourier transform module 613 transforms the symbol input signals to the frequency domain. Tone map 614 then maps each resultant tone to a frequency allocated to this user equipment. Inverse discrete Fourier transform 615 then transforms the resultant mapped tones, along with zero level tones that may be allocated to other users, back to the time domain where parallel to serial converter 616 converts the signal to a serial stream. Cyclic prefix module 617 then adds a cyclic prefix to each symbol to form the final transmission signal 620 that conforms to the slot structure FIG. 2, as further illustrated in FIG. 5.

During a transmission process, each symbol S1-S7 is sequentially input to modulator 600 to form transmission signal 620. It is important to note that cyclic prefixes {CP1, CP2, . . . , CP7} to full OFDM symbols {S1, S2, . . . , S7} are added after the IDFT, whereas cyclic prefixes {CP2.1, CP2.2, CP6.1, CP6.2} to {S2.1, S2.2, S6.1, S6.2} are added before the DFT.

In this manner, a first group of samples is created comprising at least a first and a last subgroup, wherein the last subgroup is same as the first subgroup. A second group of samples created. A transformed set of samples produced by jointly transforming the created first and second group with a discrete Fourier transform (DFT). The transformed set of samples is expanded to produce an expanded set, and the expanded set is transformed with an inverse discrete Fourier transform (IDFT) to produce an OFDM symbol with a fractional payload. The first group of samples is a reference signal (RS), which is known to the receiver before the transmission occurs, while the second group of samples is information data.

Figure 7:
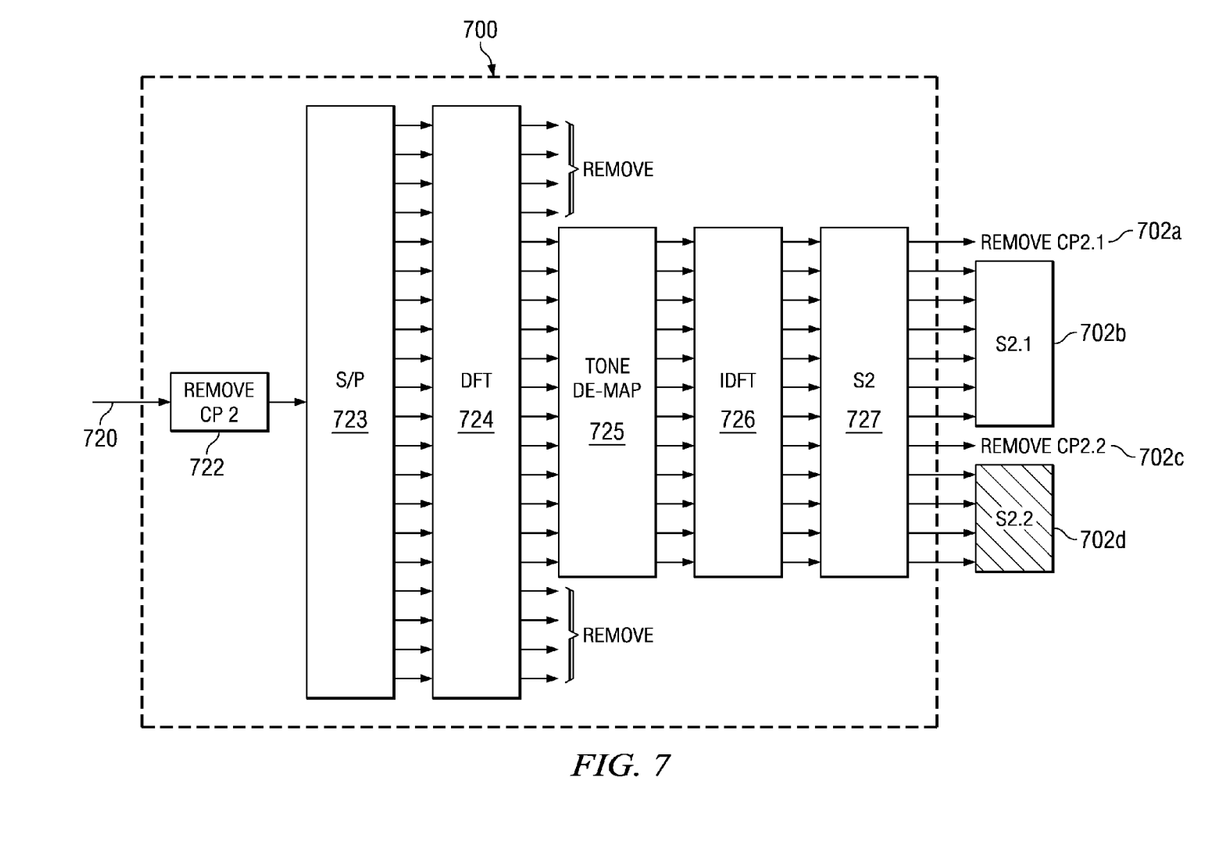
FIG. 7 is a block diagram of an illustrative demodulator for the transmission signal illustrated in FIG. 5.

FIG. 7 is a block diagram of an illustrative demodulator 700 for the transmission signal illustrated in FIG. 5. The illustrative receiver in FIG. 7 essentially undoes the operations from FIG. 6. Cyclic prefixes are first removed 722 from each whole symbol in signal 720. The resultant signal is then converted to a parallel format by serial to parallel converter 724, transformed to the frequency domain by DFT 724 where tones allocated to other user equipment is removed. The resultant set of tones is then tone de-mapped then transformed back to the time domain by IDFT 726. The resultant symbol S2 727 signal is then separated into four portions 702a-702d; CP2.1, S2.1, CP2.2, and S2.2, respectively.

Channel estimates are derived from the reference signal S2.2 (702d) and also from S6.1, which is not illustrated here. Furthermore, time-domain channel taps can be estimated as for the low-speed UEs by taking a further DFT of S2.2, demodulation in the "frequency domain," coming back to time domain with an IDFT, and zeroing taps beyond the delay spread (5 μsec). From here, channel estimates for frequency-domain equalization can be found by taking a DFT of appropriate size. All sizes involved are a multiple of {2, 3, 5}.

Furthermore, with such partition, when the length of S2 is 12, which is only one resource block (RB), the length of S2.2 then equals 4, which means that sequences of length 4 are required. Here, any solution can be adopted, including truncated or extended Zadoff-Chu, computer-generated CAZAC, etc. It ought to be noted that only a fraction of UEs in any given cell would use the piggy-backed RS in S2 and S6, and thus, their RS would collide with (random) data, from low-speed UEs, from other cells. This would provide sufficient out-of-cell interference randomization.

Clearly, it would also be feasible to use a different partition in another embodiment. For example, the RS portion of S2, which is the S2.2, could be 5/12 of the length of S2, and the S2.1 could also be 5/12 of the length of S2, where the rest would be occupied by prefixes. Such partition would also satisfy the numerology that DFT sizes are multiples of {2, 3, 5}, but the amount of channel bits carried by high and low speed UEs would be different.

A primary cause of the Doppler Effect is the UE speed, but the Doppler phenomenon can further be exacerbated and amplified by additional movements of scatterers in the propagation environment. A robust EUTRA solution, then, is to use the slot structure of FIG. 2 with one RS in S4 for low speed UE and to use the slot structure of FIG. 2 with fractional payload symbols in S2 and S6 to convey data information and reference signal information for high speed UE. The one-bit signaling required for support of flexibility of simultaneously using both slot configurations in the same cell is minimal and could be handled at the L2/L3 control level, since UE speed practically stays constant for a large number of frames. Alternatively, this signaling could also be in PDCCH. For extended CP slot-format, with only 6 OFDM symbols, the reference symbol S2 and S5 can piggy-back the RS.

Nested Multi-Rate OFDMA and SC-OFDMA Systems

In another embodiment of the invention, more than one OFDMA sub-system may be multiplexed, where different OFDMA sub-systems can have different OFDMA symbol rates. OFDMA symbol rate is inversely proportional to the tone spacing. There are M different Sub-Systems, where a particular Sub-System is indexed by "m," and it holds that $1 \le m \le M$. All Sub-Systems have a common base rate, which can be achieved by an "inner" IDFT [Inverse Discrete Fourier Transform] of one common size, which is employed across all Sub-Systems. Thus, there is one common "base rate," which is shared across all Sub-Systems. Furthermore, there can be one optional common-length cyclic prefix (CP), or alternatively, guard time (GT), inserted after the common-length IDFT. Different Sub-Systems can be multiplexed using different Tone Mappings, which feed into the IDFT of the common rate. Each Sub-System "m" can have a distinct Tone Map "m." Then, each Sub-System, for example, Sub-System "m," can have a unique "derived rate," which is specific for that Sub-System "m."

Figure 8:
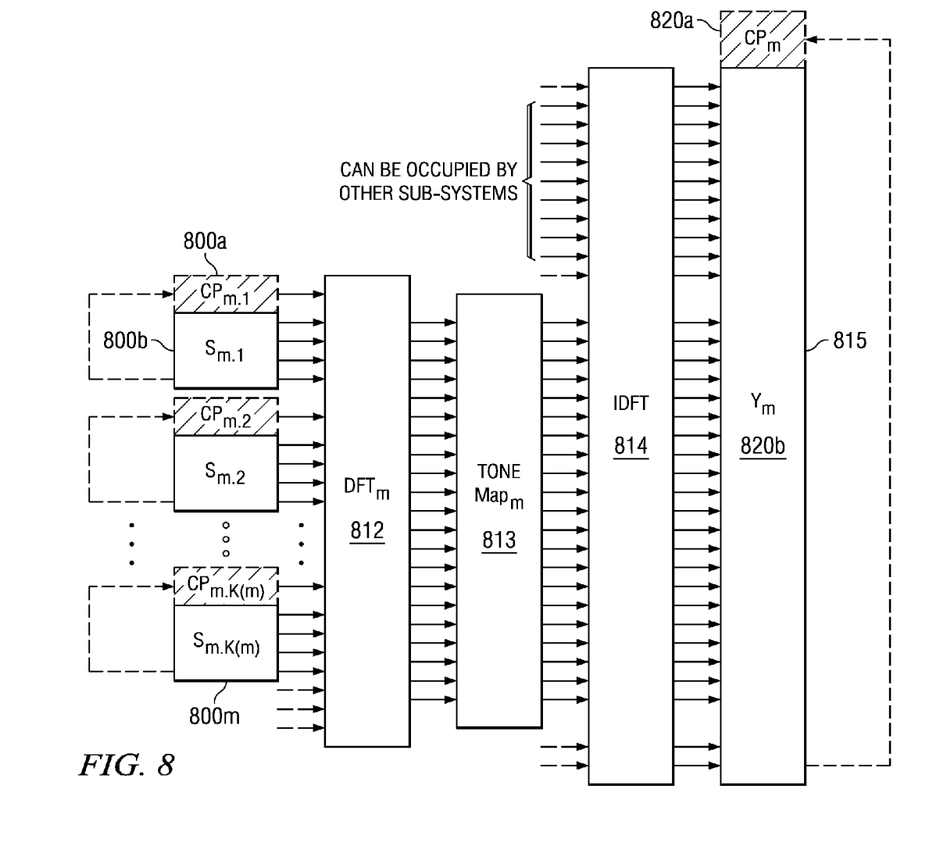
FIG. 8 is a block diagram of a modulator for nested multi-rate SC-OFDMA system.

FIG. 8 is a block diagram of a modulator for nested multi-rate SC-OFDMA system. In order to specify Sub-System ("m") specific "derived rate," a DFTm 812 is employed prior to the Tone Map "m" 813. DFTm 812 can have a length which is specific to Sub-System "m." The DFTm feeds into the IDFT 814 of common size via the Sub-System specific Tone Map "m" 813. Consequently, the signal prior to the Sub-System specific DFTm can be regarded as a time-domain signal. The signal which is fed into the Sub-System specific DFTm can comprise from several or more components 800a, 800b-800m. In particular, the signal which feeds into the DFTm 812 can include K(m) different signals, and K(m) different cyclic prefixes to those signals. For example, signal Sm.1 800a has a cyclic prefix CPm.1 800b; signal Sm.2 has a cyclic prefix CPm.2 etc and finally, the last signal Sm.K(m) 800m has a cyclic prefix CPm.K(m). Each cyclic prefix is created for just its associated signal using known techniques. All said cyclic prefixes may or may not be present, or they can alternatively be a simple guard time. All cyclic prefixes and signals CPm.1; Sm.1; CPm.2; Sm.2; etc CPm.K(m); Sm.K(m) are concatenated and fed as an input to the Sub-System specific IDFTm 814. Thus, the Sub-System "m" generates K(m) symbols for each single symbol at the "base rate." Consequently, since K(m) can clearly differ between sub-systems, the "derived rates" can be different across Sub-Systems.

In the uplink of wireless communication systems, each user can use either the entire Sub-System or a part of it. However, it is not precluded that a user uses more than one Sub-System. Same holds for downlink of wireless communication systems. The invention applies broadly, and is not restricted to wireless communication systems only.

Referring still to FIG. 8, symbols Sm.1; Sm.2; etc Sm.K(m) can be modulated symbols, like PSK or QAM, or symbols which employ any other modulation. Furthermore, they can be reference symbols, which can be used for coherent data demodulation, for channel sounding, etc. Cyclic prefixes [CPm.1; CPm.2; etc CPm.K(m)] or alternatively, guard times, can be inserted to each of the said symbols Sm.1; Sm.2; etc Sm.K(m) as shown in FIG. 8. In different embodiments, these symbols may be of different sizes. Note that, CPm.k is just the last group of samples from Sm.k. All of these signals are concatenated and are used as an input to the Sub-System specific DFTm 812. Other inputs to the DFTm are not precluded, and are represented by dashed arrows in FIG. 8. The output of DFTm 810 is mapped onto the IDFT via the Tone Map "m." The IDFT size can be common for all Sub-Systems. Tone maps between different Sub-Systems may or may not be separated by (zeroed-out) guard tones, as shown with the dashed arrow in FIG. 8. Guard tones can also be inserted at the edges. Cyclic prefix (CPm) 820a, or alternatively, guard time, can be inserted at the output of the IDFT to cover the entire output symbol 820b, as shown in FIG. 8. The size of the CPm 20a may or may not be common for all Sub-Systems. Numbers of arrows are only exemplary and representative, and are not meant to restrict the scope of the invention in any way.

Figure 9:
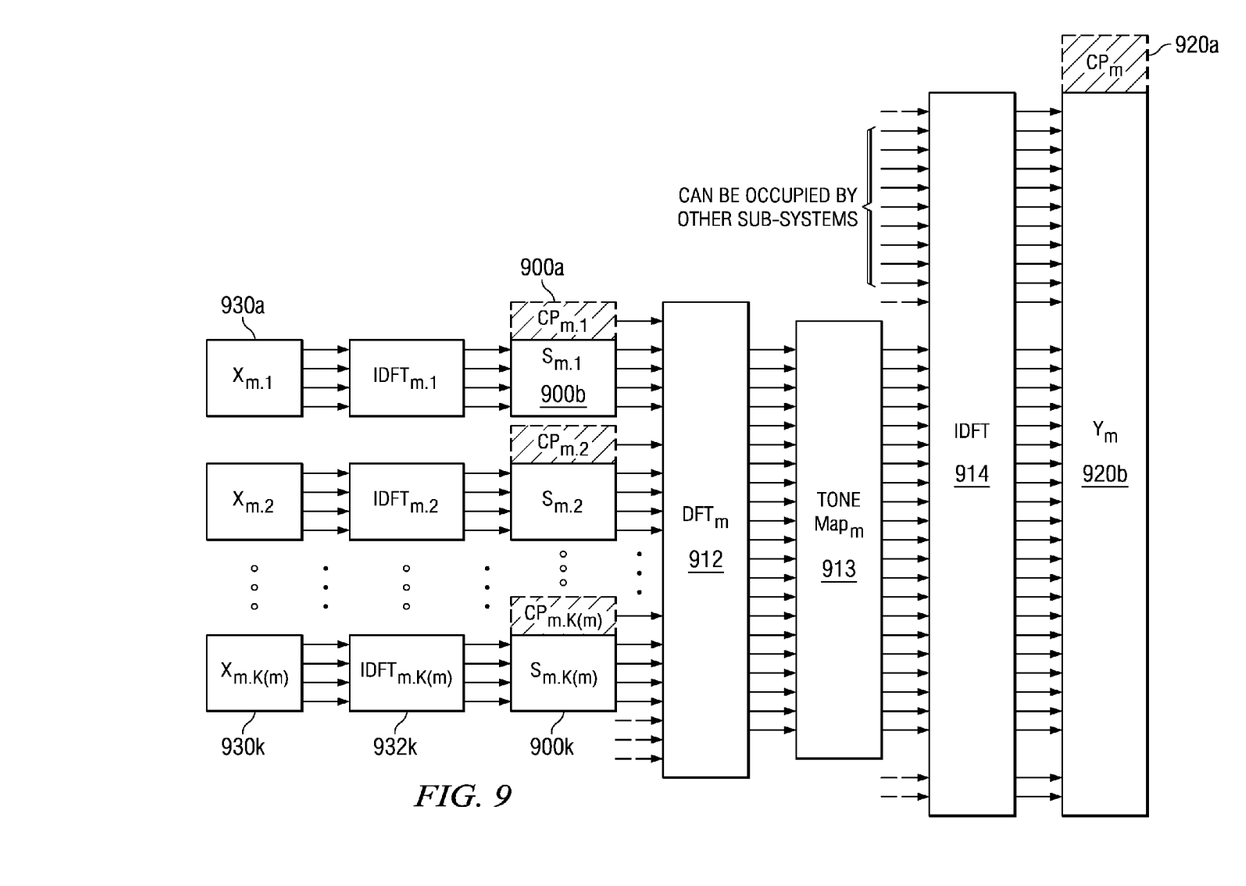
FIG. 9 is a block diagram of a modulator for nested multi-rate OFDMA system.

FIG. 9 is a block diagram of a modulator for nested multi-rate OFDMA system. Here, FIG. 9 shows a transmitter diagram for Sub-System "m." Symbols Xm.1; Xm.2; etc Xm.K(m) (indicated generally at 930a-930k) can be modulated symbols, like PSK or QAM, or symbols which employ any other modulation. Furthermore, they can be reference symbols, which can be used for coherent data demodulation, for channel sounding, etc. Certain components of symbols Xm.1; Xm.2; etc Xm.K(m) can also be zeroes, because those tones can be used by other users, or can be PAPR reducing signals, or anything else. Each symbol Xm.k is transformed using IDFTm.k, generally indicated at 932k, and all of these transforms (or symbols) may not be of the same size. The IDFTm.k transform of the symbol Xm.k produces Sm.k as generally indicated at 900k. Then, cyclic prefix CPm.k, or alternatively, guard time, can be inserted to the Sm.k as illustrated indicated generally at 900a, 900b. This is similar to the SC-OFDMA modulator of FIG. 8. All of these signals [CPm.1; Sm.1; CPm.2; Sm.2; etc CPm.K(m); Sm.K(m)] are concatenated and are used as an input to the Sub-System specific DFTm 912. Other inputs to DFTm 912 are not precluded, and are represented by dashed arrows in FIG. 9. The output of DFTm 912 is mapped onto IDFT 914 via Tone Map "m" 913. The IDFT size can be common for all Sub-Systems. Tone maps between different Sub-Systems may or may not be separated by zeroed-out guard tones, as shown with the dashed arrow in FIG. 9. Guard tones can also be inserted at the edges. Cyclic prefix (CPm) 920a, or alternatively, guard time, can be inserted at the output of the IDFT to cover the entire symbol 920b. The size of CPm 920a may or may not be common for all Sub-Systems. Numbers of arrows are only exemplary and representative, and are not meant to restrict the scope of the invention in any way.

Combined Nested Multi-Rate OFDMA and SC-OFDMA System

It is clear that, at the derived rate, some symbols Sm.k 900k can be generated using IDFTm.k 932k, as shown generally in FIG. 9, whereas other symbols Sm.k don't need to be generated using IDFTm.k. These can be stand-alone generated symbols Sm.k as in FIG. 8. Such system is a combination of Nested Multi-Rate OFDMA and SC-OFDMA Systems.

Figure 10:
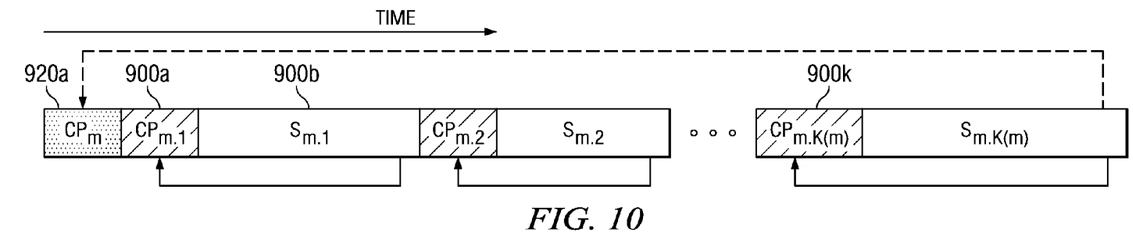
FIG. 10 is timing diagram for nested multi-rate SC-OFDMA and OFDMA systems.

FIG. 10 is timing diagram for nested multi-rate SC-OFDMA and OFDMA systems. Note that there are two types of cyclic prefixes. As described above, CPm.k is a cyclic prefix to Sm.k but it is inserted before the DFTm. As before, $1 \le k \le K(m)$. The CPm is a cyclic prefix to Ym 920b which is inserted after IDFT. So, cyclic prefix insertions in FIG. 10 may be in different rates. At times, DFTm and IDFT cancel each other, and in those cases, they can be omitted, and cyclic prefixes inserted directly.

Applications

The application of the described scheme becomes clear in the multi-user scenario. Typically, in any given cellular system, there are multiple users. These multiple users can have disparate Doppler spreads, delay spreads, or any other disparate characteristics of individual propagation channels. Consequently, parameters of each Sub-System can be tailored to the channel characteristics of its users. For example, if user or users with lower delay spreads are located in the Sub-System "m," then that Sub-System can have lower prefix duration [of the Sub-System specific cyclic prefix]. Similarly, if user or users with lower Doppler spreads are located in a particular Sub-System, then that particular Sub-System can have longer symbols [referring to Sub-System specific symbols, of the "derived rate"]. Clearly, as users' propagation environments change, they can be moved to different Sub-Systems, and/or Sub-Systems themselves can be re-configured. Thus, the described architecture offers enough flexibility to allow for tuning the symbol parameters to individual users propagation conditions.

Figure 11:
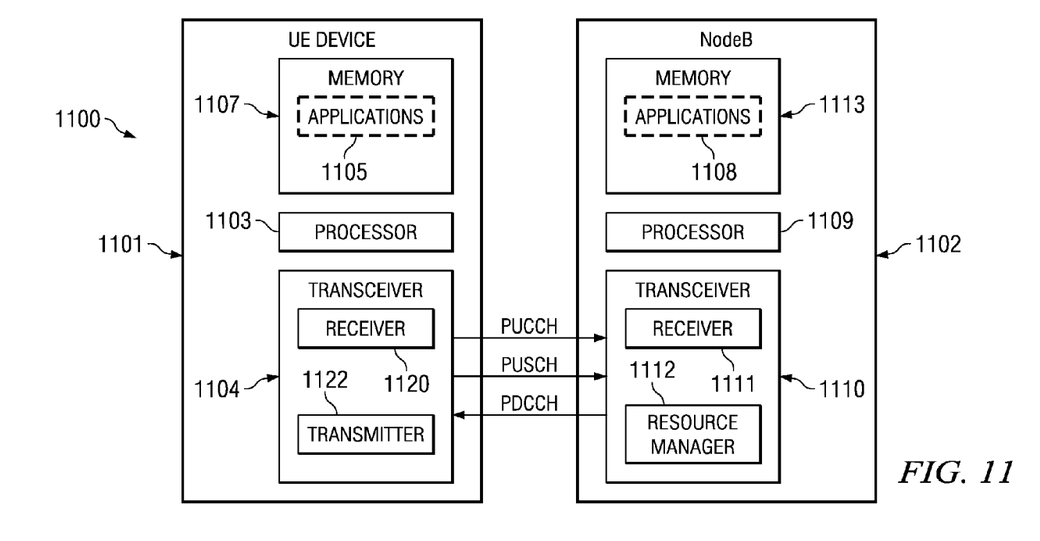
FIG. 11 is a block diagram of a Node B and a User Equipment for use in the network system of FIG. 1.

FIG. 11 is a block diagram illustrating operation of an eNB and a mobile UE in the network system of FIG. 1. As shown in FIG. 11, wireless networking system 1100 comprises a mobile UE device 1101 in communication with an eNB 1102. The mobile UE device 1101 may represent any of a variety of devices such as a server, a desktop computer, a laptop computer, a cellular phone, a Personal Digital Assistant (PDA), a smart phone or other electronic devices. In some embodiments, the electronic mobile UE device 1101 communicates with the eNB 1102 based on a LTE or E-UTRAN protocol. Alternatively, another communication protocol now known or later developed can be used.

As shown, the mobile UE device 1101 comprises a processor 1103 coupled to a memory 1107 and a Transceiver 1104. The memory 1107 stores (software) applications 1105 for execution by the processor 1103. The applications 1105 could comprise any known or future application useful for individuals or organizations. As an example, such applications 1105 could be categorized as operating systems (OS), device drivers, databases, multimedia tools, presentation tools, Internet browsers, e-mailers, Voice-Over-Internet Protocol (VoIP) tools, file browsers, firewalls, instant messaging, finance tools, games, word processors or other categories. Regardless of the exact nature of the applications 1105, at least some of the applications 1105 may direct the mobile UE device 1101 to transmit UL signals to the eNB (base-station) 1102 periodically or continuously via the transceiver 1104. In at least some embodiments, the mobile UE device 1101 identifies a Quality of Service (QoS) requirement when requesting an uplink resource from the eNB 1102. In some cases, the QoS requirement may be implicitly derived by the eNB 1102 from the type of traffic supported by the mobile UE device 1101. As an example, VoIP and gaming applications often involve low-latency uplink (UL) transmissions while High Throughput (HTP)/Hypertext Transmission Protocol (HTTP) traffic can involve high-latency uplink transmissions.

Transceiver 1104 includes uplink logic which may be implemented by execution of instructions that control the operation of the transceiver. Some of these instructions may be stored in memory 1107 and executed when needed. As would be understood by one of skill in the art, the components of the Uplink Logic may involve the physical (PHY) layer and/or the Media Access Control (MAC) layer of the transceiver 1104. Transceiver 1104 includes one or more receivers 1120 and one or more transmitters 1122. The transceivers(s) may be embodied to process a transmission signal with the slot structure as described with respect to FIGS. 2-10. In particular, as described above, a transmission signal comprises at least one data symbol and at least one RS symbol. An exemplary transmission signal comprising five data symbols and two RS symbols is shown in FIG. 2. For low velocity UE, a single RS is placed in symbol S4. For high velocity UE, two fractional payload symbols convey data information and reference signal information in symbols S2 and S6.

As shown in FIG. 11, the eNB 1102 comprises a Processor 1109 coupled to a memory 1113 and a transceiver 1110. The memory 1113 stores applications 1108 for execution by the processor 1109. The applications 1108 could comprise any known or future application useful for managing wireless communications. At least some of the applications 1108 may direct the base-station to manage transmissions to or from the user device 1101.

Transceiver 1110 comprises an uplink Resource Manager 1112, which enables the eNB 1102 to selectively allocate uplink PUSCH resources to the user device 1101. As would be understood by one of skill in the art, the components of the uplink resource manager 1112 may involve the physical (PHY) layer and/or the Media Access Control (MAC) layer of the transceiver 1110. Transceiver 1110 includes a Receiver 1111 for receiving transmissions from various UE within range of the eNB and transmitters for transmitting data and control information to the various UE within range of the eNB.

Uplink resource manager 1112 executes instructions that control the operation of transceiver 1110. Some of these instructions may be located in memory 1113 and executed when needed. Resource manager 1112 controls the transmission resources allocated to each UE that is being served by eNB 1102 and broadcasts control information via the physical downlink control channel PDCCH. The transceivers(s) may be embodied to process a transmission signal with the slot structure as described with respect to FIGS. 2-10. In particular, as described above, a transmission signal comprises at least one data symbol and at least one RS symbol. An exemplary transmission signal received from UE 1101 on the PUSCH comprises five data symbols and two RS symbols as shown in FIG. 2. For low velocity UE, a single RS is placed in symbol S4. For high velocity UE, two fractional payload symbols convey data information and reference signal information in both symbols S2 and S6. The data throughput rate is the same for both modes of transmission while channel estimation for data demodulation is improved for high velocity UE by having two RS signals included in a single slot structure, provided these pre-defined/un-modulated reference signals are known to both the transmitter and the receiver.

The one-bit signaling required for support of flexibility of simultaneously using both slot configurations in the same cell is minimal and may be handled at the L2/L3 control level, since UE speed practically stays constant for a large number of frames. Alternatively, this signaling could also be in PDCCH. For extended CP slot-format, with only 6 OFDM symbols, the reference symbol S2 and S5 can piggy-back the RS.

Figure 12:
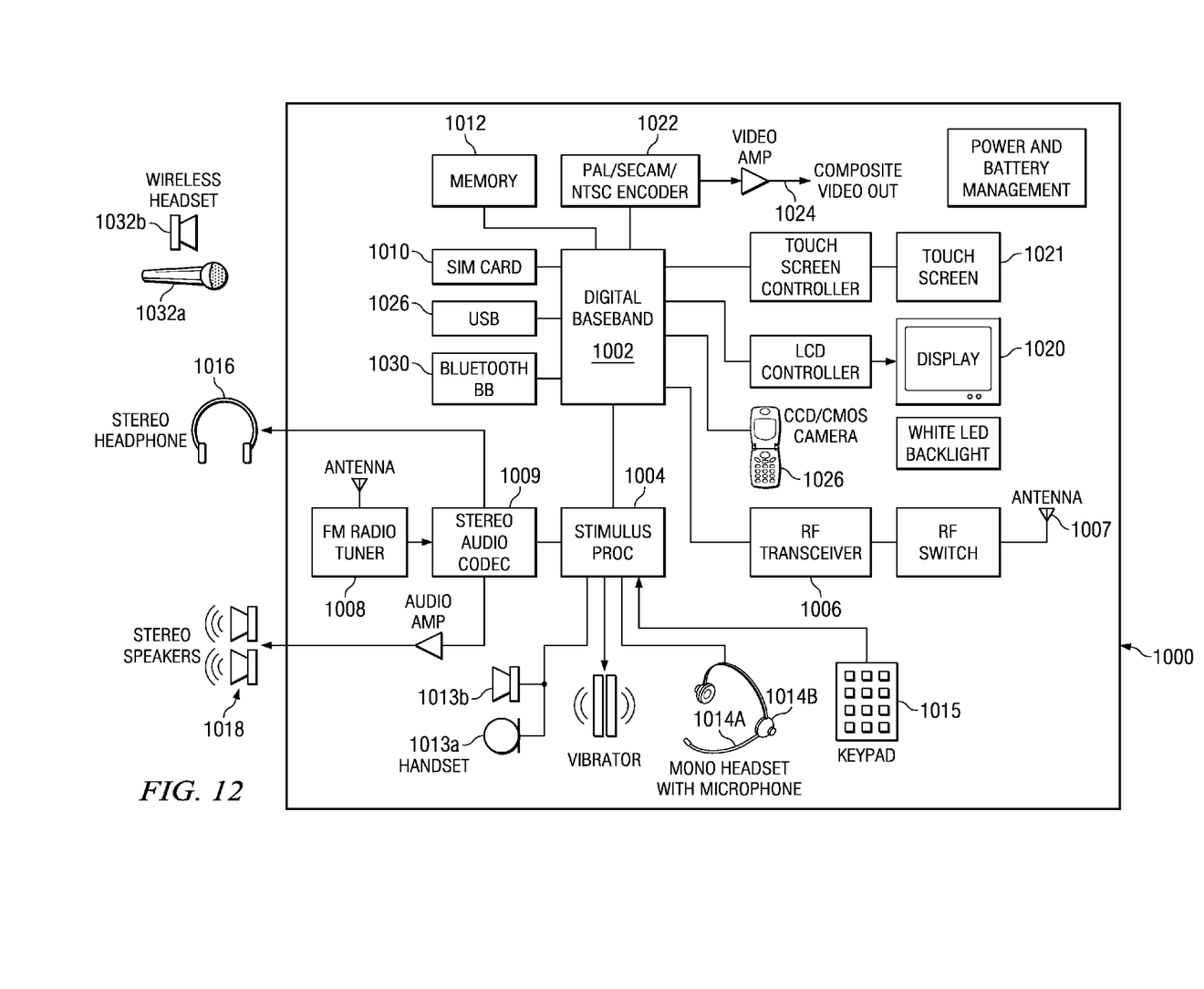
FIG. 12 is a block diagram of a cellular phone for use in the network of FIG. 1.

FIG. 12 is a block diagram of mobile cellular phone 1000 for use in the network of FIG. 1. Digital baseband (DBB) unit 1002 can include a digital processing processor system (DSP) that includes embedded memory and security features. Stimulus Processing (SP) unit 1004 receives a voice data stream from handset microphone 1013a and sends a voice data stream to handset mono speaker 1013b. SP unit 1004 also receives a voice data stream from microphone 1014*a* and sends a voice data stream to mono headset 1014*b*. Usually, SP and DBB are separate ICs. In most embodiments, SP does not embed a programmable processor core, but performs processing based on configuration of audio paths, filters, gains, etc being setup by software running on the DBB. In an alternate embodiment, SP processing is performed on the same processor that performs DBB processing. In another embodiment, a separate DSP or other type of processor performs SP processing.

RF transceiver 1006 includes a receiver for receiving a stream of coded data frames and commands from a cellular base station via antenna 1007 and a transmitter for transmitting a stream of coded data frames to the cellular base station via antenna 1007. Transmission of the PUSCH data is performed by the transceiver using the PUSCH resources designated by the serving eNB. In some embodiments, frequency hopping may be implied by using two or more bands as commanded by the serving eNB. In this embodiment, a single transceiver can support multi-standard operation (such as EUTRA and other standards) but other embodiments may use multiple transceivers for different transmission standards. Other embodiments may have transceivers for a later developed transmission standard with appropriate configuration. RF transceiver 1006 is connected to DBB 1002 which provides processing of the frames of encoded data being received and transmitted by the mobile UE unit 1000.

The EUTRA defines SC-FDMA (via DFT-spread OFDMA) as the uplink modulation. The basic SC-FDMA DSP radio can include discrete Fourier transform (DFT), resource (i.e. tone) mapping, and IFFT (fast implementation of IDFT) to form a data stream for transmission. To receive the data stream from the received signal, the SC-FDMA radio can include DFT, resource de-mapping and IFFT. The operations of DFT, IFFT and resource mapping/de-mapping may be performed by instructions stored in memory 1012 and executed by DBB 1002 in response to signals received by transceiver 1006.

The transceivers(s) are be embodied to process a transmission signal with the slot structure as described with respect to FIGS. 2-10. In particular, as described above, a transmission signal comprises at least one data symbol and at least one RS symbol. An exemplary transmission signal comprising five data symbols and two RS symbols is shown in FIG. 2. For low velocity UE, a single RS is placed in symbol S4. For high velocity UE, two fractional payload symbols convey data information and reference signal information in both symbols S2 and S6. The data throughput rate is the same for both modes of transmission while channel estimation for data demodulation is improved for high velocity UE by having two RS signals included in a single slot structure, provided these pre-defined/un-modulated reference signals are known to both the transmitter and the receiver.

DBB unit 1002 may send or receive data to various devices connected to universal serial bus (USB) port 1026. DBB 1002 can be connected to subscriber identity module (SIM) card 1010 and stores and retrieves information used for making calls via the cellular system. DBB 1002 can also connected to memory 1012 that augments the onboard memory and is used for various processing needs. DBB 1002 can be connected to Bluetooth baseband unit 1030 for wireless connection to a microphone 1032*a* and headset 1032*b* for sending and receiving voice data. DBB 1002 can also be connected to display 1020 and can send information to it for interaction with a user of the mobile UE 1000 during a call process. Display 1020 may also display pictures received from the network, from a local camera 1026, or from other sources such as USB 1026.

DBB 1002 may also send a video stream to display 1020 that is received from various sources such as the cellular network via RF transceiver 1006 or camera 1026. DBB 1002 may also send a video stream to an external video display unit via encoder 1022 over composite output terminal 1024. Encoder unit 1022 can provide encoding according to PAL/SECAM/NTSC video standards.

As used herein, the terms "applied," "coupled," "connected," and "connection" mean electrically connected, including where additional elements may be in the electrical connection path. "Associated" means a controlling relationship, such as a memory resource that is controlled by an associated port.

While the invention has been described with reference to illustrative embodiments, this description is not intended to be construed in a limiting sense. Various other embodiments of the invention will be apparent to persons skilled in the art upon reference to this description. For example, a larger or smaller number of symbols then described herein may be used in a slot.

It is therefore contemplated that the appended claims will cover any such modifications of the embodiments as fall within the true scope and spirit of the invention.

What is claimed is:

1. A method of communication comprising the steps of:
receiving user data for transmission;
placing a first reference signal (RS) and some of the user data onto a first symbol portion of a slot of an orthogonal frequency division multiple access (OFDMA) signal;
placing a second reference signal (RS) and other of the user data onto a second symbol portion of the slot of the orthogonal frequency division multiple access (OFDMA) signal, at least one additional symbol portion of the slot separating the first and second symbols; and
transmitting a radio frequency signal modulated corresponding to the symbol portions of the slot of the orthogonal frequency division multiple access (OFDMA) signal.

2. The method of claim 1, wherein:
said first reference signal (RS) and some of the user data are concatenated in a first order.

3. The method of claim 1, wherein:
said step of transmitting a radio frequency signal includes receiving symbol portions of the slot of the orthogonal frequency division multiple access (OFDMA) signal, transforming the symbol portions into a frequency domain signal via a discrete Fourier transform, mapping each transformed symbol portion to a tone selected from a tone map, transforming the selected tone into a time domain signal via an inverse discrete Fourier transform, converting each time domain signal into a serial format, adding a cyclic prefix to each symbol portion; and
adding corresponding cyclic prefixes to the first reference signal (RS) and some of the user data placed onto the symbol portion before said step of transmitting.

4. The method of claim 1, wherein:
said step of placing the first reference signal (RS) and some of the user data onto a first symbol portion of a slot of an orthogonal frequency division multiple access (OFDMA) signal includes concatenating the first reference signal (RS) and some of the user data in a first order.

5. The method of claim 1, wherein:
said step of placing the first reference signal (RS) and some of the user data onto a first symbol portion of a slot of an orthogonal frequency division multiple access (OFDMA) signal includes concatenating the first reference signal (RS) and some of the user data in a first order;

said step of placing a second reference signal (RS) and other of the user data onto a second symbol portion of the slot of the orthogonal frequency division multiple access (OFDMA) signal includes concatenating the second reference signal (RS) and the other of the user data in a second order.

6. The method of claim 5, wherein the first order is opposite to the second order.

7. The method of claim 1, further comprising adding a cyclic prefix to each symbol portion.

8. The method of claim 1, further comprising adding a corresponding cyclic prefix to at least one of the first reference signal (RS) and some of the user data.

9. The method of claim 8, further comprising adding a corresponding cyclic prefix to at least one of the second reference signal (RS) and other of the user data.

10. The method of claim 1, further comprising adding a corresponding cyclic prefix to at least one of the second reference signal (RS) and other of the user data.

11. The method of claim 10, further comprising adding a corresponding cyclic prefix to at least one of the first reference signal (RS) and some of the user data.

12. The method of claim 1, further comprising adding a corresponding cyclic prefix to the first symbol portion and adding a corresponding cyclic prefix to the second symbol portion.

13. The method of claim 12, further comprising adding a corresponding cyclic prefix to said some of the user data and adding a corresponding cyclic prefix to said other of the user data.

14. The method of claim 1, further comprising adding a corresponding cyclic prefix to the some of the user data.

15. The method of claim 1, further comprising adding a corresponding cyclic prefix to the other of the user data.

16. The method of claim 1, further comprising adding a corresponding cyclic prefix to said some of the user data and adding a corresponding cyclic prefix to the first reference signal (RS).

17. The method of claim 1, wherein a length of a portion of the first symbol portion for the some of the user data is larger than the length of a portion of the first symbol portion for the reference signal (RS).

18. The method of claim 1, wherein a length of a portion of the second symbol portion for the some of the user data is larger than the length of a portion of the second symbol portion for the reference signal (RS).

19. The method of claim 1, wherein:
a length of a portion of the first symbol portion for the some of the user data is larger than the length of a portion of the first symbol portion for the first reference signal (RS); and
a length of a portion of the second symbol portion for the some of the user data is larger than the length of a portion of the second symbol portion for the second reference signal (RS).

20. The method of claim 1, wherein at least two additional symbol portions of the slot separate the first and second symbols.

21. The method of claim 1, wherein at least three additional symbol portions of the slot separate the first and second symbol portions.

22. The method of claim 1, further comprising a cyclic prefix separating the first reference signal (RS) from the some of the user data.

23. The method of claim 1, further comprising a cyclic prefix separating the second reference signal (RS) from the other of the user data.

24. The method of claim 1, wherein the slot comprises at least three symbol portions.

25. The method of claim 1, wherein the slot comprises seven symbol portions.

26. The method of claim 25, wherein each symbol portion comprises an OFDMA symbol.

27. The method of claim 1, wherein the slot is used for transmitting uplink control information using the physical uplink control channel (PUCCH), as defined by the 3GPP working groups (WG), for evolved universal terrestrial radio access (EUTRA).

28. The method of claim 1, wherein the at least one additional symbol portion of the slot separating the first and second symbols does not contain a reference signal (RS).

29. An apparatus for transmitting in a cellular communication system comprising:
circuitry for generating user data for transmission;
circuitry for placing a first reference signal (RS) and some of the user data onto a first symbol portion of a slot of an orthogonal frequency division multiple access (OFDMA) signal;
circuitry for placing a second reference signal (RS) and other of the user data onto a second symbol portion of the slot of the orthogonal frequency division multiple access (OFDMA) signal, at least one additional symbol portion of the slot separating the first and second symbols;
circuitry for transmitting a radio frequency signal modulated corresponding to the symbol portions of the slot of the orthogonal frequency division multiple access (OFDMA) signal.

30. The apparatus of claim 29, wherein:
said circuitry for placing a second reference signal (RS) and other of the user data onto a second symbol portion of the slot of the orthogonal frequency division multiple access (OFDMA) signal is further operable to concatenate the first reference signal (RS) and some of the user data in a first order, and concatenate the second reference signal (RS) and other of the user data in a second order;
said transmitting circuitry further operable to place the concatenated first reference signal and some of the user data of the first order onto the first symbol portion, and place the second concatenated reference signal and other of the user data of the second order onto the second symbol portion.

31. The apparatus of claim 29, wherein:
said circuitry for placing a first reference signal (RS) and some of the user data onto a first symbol portion of a slot of an orthogonal frequency division multiple access (OFDMA) signal is further operable to add corresponding cyclic prefixes to the first reference signal (RS);
said circuitry for placing a second reference signal (RS) and other of the user data onto a second symbol portion of the slot of the orthogonal frequency division multiple access (OFDMA) signal is further operable to add corresponding cyclic prefixes to the second reference signal (RS); and
said transmitting circuitry further including receiving circuitry for receiving symbol portions of the slot of the orthogonal frequency division multiple access (OFDMA) symbol sequentially, a discrete Fourier transformer for transforming symbol portions into a frequency domain signal via a discrete Fourier transform, a mapper for mapping each transformed symbol portion to a tone selected from a tone map, an inverse discrete Fourier transformer for transforming the selected tone into a time domain signal via an inverse discrete Fourier transform, and a parallel to serial converter for converting each time domain signal into a serial format.

32. The apparatus of claim 29, further comprising circuitry for adding a cyclic prefix to each symbol portion.

33. The apparatus of claim 29, further comprising circuitry for adding a corresponding cyclic prefix to the reference signal (RS) of the first reference signal (RS) and some of the user data.

34. The apparatus of claim 29, further comprising circuitry for adding a corresponding cyclic prefix to the second reference signal (RS) and other of the user data.

35. The apparatus of claim 29, further comprising circuitry for adding a corresponding cyclic prefix to the first reference signal (RS) and some of the user data and adding a corresponding cyclic prefix to the second reference signal (RS) and other of the user data.

36. The apparatus of claim 29, further comprising circuitry for adding a corresponding cyclic prefix to the some of the user data.

37. The apparatus of claim 29, further comprising circuitry for adding a corresponding cyclic prefix to the other of the user data.

38. The apparatus of claim 29, further comprising circuitry for adding a corresponding cyclic prefix to the some of the user data and adding a corresponding cyclic prefix to the other of the user data.

39. The apparatus of claim 29, wherein a length of a portion of the first symbol portion for the some of the user data is larger than the length of a portion of the first symbol portion for the first reference signal (RS).

40. The apparatus of claim 29, wherein a length of a portion of the second symbol portion for the some of the user data is larger than the length of a portion of the second symbol portion for the second reference signal (RS).

41. The apparatus of claim 29, wherein:
a length of a portion of the first symbol portion for the some of the user data is larger than the length of a portion of the first symbol portion for the first reference signal (RS); and
a length of a portion of the second symbol portion for the some of the user data is Larger than the length of a portion of the second symbol portion for the second reference signal (RS).

42. The apparatus of claim 29, wherein at least two additional symbol portions of the slot separate the first and second symbol portions.

43. The apparatus of claim 29, wherein at least three additional symbol portions of the slot separate the first and second symbol portions.

44. The apparatus of claim 29, further comprising a cyclic prefix separating the first reference signal (RS) from the some of the user data.

45. The apparatus of claim 29, further comprising a cyclic prefix separating the second reference signal (RS) from the other of the user data.

46. The apparatus of claim 29, wherein the slot comprises at least three symbol portions.

47. The apparatus of claim 29, wherein the slot comprises seven symbol portions.

48. The apparatus of claim 47, wherein each symbol portion comprises an OFDMA symbol.

49. The apparatus of claim 29, wherein the slot is used for transmitting uplink control information using the physical uplink control channel (PUCCH), as defined by the 3GPP working groups (WG), for evolved universal terrestrial radio access (EUTRA).

50. A method of communication comprising the steps of:
placing a first reference signal (RS) and some user data onto a first symbol portion of a slot of an orthogonal frequency division multiple access (OFDMA) signal;
placing a second reference signal (RS) and other user data onto a second symbol portion of the slot of the orthogonal frequency division multiple access (OFDMA) signal, at least one additional symbol portion of the slot separating the first and second symbol portions; and
transmitting a radio frequency signal modulated corresponding to the symbol portions of the slot of the orthogonal frequency division multiple access (OFDMA) signal.

51. The apparatus of claim 29, wherein the at least one additional symbol portion of the slot separating the first and second symbols does not contain a reference signal (RS).

* * * * *